(12) United States Patent
Alhourani (10) Patent No.: US 10,154,896 B2
(45) Date of Patent: Dec. 18, 2018

(54) CORNEAL FIXATION OF AN INTRAOCULAR LENS

(71) Applicant: Rakan Elias Jamil Alhourani, Alfuhais (JO)

(72) Inventor: Rakan Elias Jamil Alhourani, Alfuhais (JO)

(*) Notice: Subject to any disclaimer, the term of this patent is extended or adjusted under 35 U.S.C. 154(b) by 0 days.

(21) Appl. No.: 15/261,908

(22) Filed: Sep. 10, 2016

(65) Prior Publication Data

US 2018/0071081 A1 Mar. 15, 2018

(51) Int. Cl.
*A61F 2/14* (2006.01)
*A61F 2/16* (2006.01)

(52) U.S. Cl.
CPC .... *A61F 2/1605* (2015.04); *A61F 2002/1689* (2013.01); *A61F 2002/16902* (2015.04); *A61F 2220/0041* (2013.01)

(58) Field of Classification Search
CPC .. A61F 2/142; A61F 2/147; A61F 2/14; A61F 9/007
See application file for complete search history.

(56) References Cited

U.S. PATENT DOCUMENTS 8,486,140 B2 * 7/2013 Willis .................. A61F 2/1602
623/5.14

* cited by examiner

*Primary Examiner* — David H Willse
*Assistant Examiner* — Tiffany Shipmon (57) ABSTRACT

A method to fixate an intraocular lens by connecting it with the cornea or the limbus of the eye, using wedges that are implanted through the cornea or the limbus till they reach and attach and stabilize an implanted intraocular lens.

1 Claim, 9 Drawing Sheets

CORNEAL FIXATION OF AN INTRAOCULAR LENS

CROSS-REFERENCES TO RELATED APPLICATIONS

Not Applicable

STATEMENT REGARDING FEDERALLY SPONSORED RESEARCH OR DEVELOPMENT

Not Applicable

STATEMENT REGARDING PRIOR DISCLOSURES BY THE INVENTOR OR A JOINT INVENTOR

Not Applicable

FIELD OF THE INVENTION

The present invention is a new method that fixates an intraocular lens, by attaching it to the cornea or the limbus using corneal/limbal wedges.

BACKGROUND OF THE INVENTION

During any cataract surgery we may get a posterior capsular rupture complication, which will prevent us to implant an intraocular lens adequately in the bag or sometimes even in the sulcus, so we may implant it in the anterior chamber of the globe or bring the patient later to implant a scleral fixated intraocular lens or keep the eye with no intraocular lens. Some of complications in those situations are: for the scleral fixation the lens is not stable, and for anterior chamber intraocular lens the lens is not completely fixed so it moves and causes mechanical harm to the angle that causes glaucoma, and causes harm to the endothelium which eventually causes decompensation and its complications. This invention of corneal/limbal fixation using corneal/limbal wedges (Elias wedges) will stabilize and fixate an intraocular lens in a fixed distance between the lens and the cornea, which will prevent any mechanical harm or injury to the endothelium and further prevent the vitreous— if any—to contact and damage the endothelium, and this process will prevent any mechanical harm or destruction to the trabecular meshwork at the anterior chamber angle, which will decrease the risk of glaucoma for the anterior chamber intraocular lenses. In addition, this invention of corneal/limbal fixation will stabilize an intraocular lens almost 100 percent in relation to the cornea in all directions, by this we may expand the range of treating high refractive errors, high astigmatism and even irregular refractive errors of the cornea or the crystalline lens, using corneal/limbal fixed phakic intraocular lens. So this invention of corneal/limbal fixation using corneal/limbal wedges (Elias wedges) can be used for phakic intraocular lenses, secondary intraocular lenses and pseudophakic intraocular lenses. Furthermore corneal/limbal wedges (Elias wedges) of this invention can be used to stabilize any device implanted in the anterior chamber such as tubes of glaucoma valves.

SUMMARY OF THE INVENTION

The present invention is a method that fixates and stabilizes an intraocular lens by using corneal/limbal wedges (Elias wedges), which extend from the cornea or the limbus and lodge into the haptics of an intraocular lens.

DETAILED DESCRIPTION OF THE INVENTION

This new invention of corneal/limbal fixation of an intraocular lens has two components: the modified intraocular lens and the corneal/limbal wedge (Elias wedge).

Figure 1:
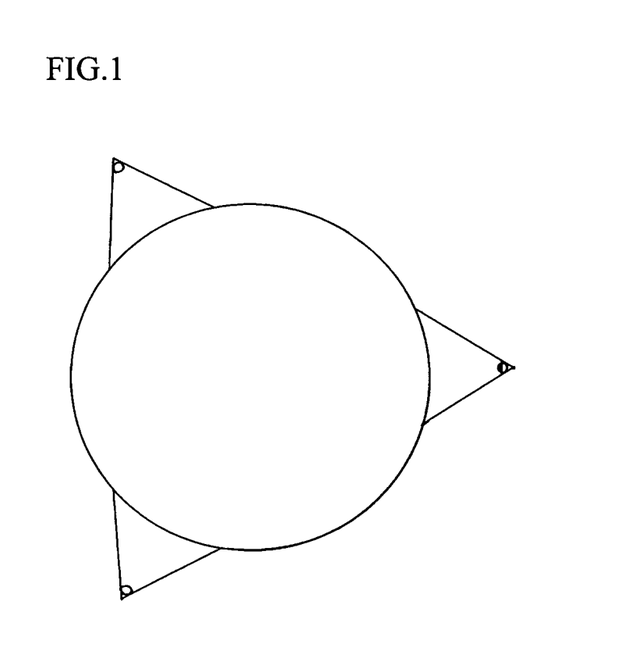
FIG. 1: Modified intraocular lens.

First: the modified intraocular lens FIG. 1, which has an optic part and modified haptics (plate haptics or arms).

Figure 2:
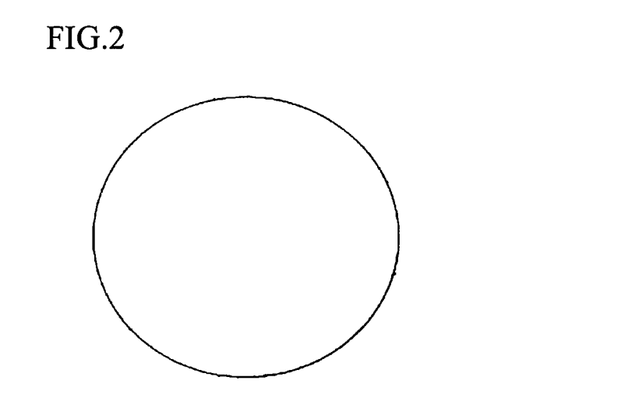
FIG. 2: The first part of the modified intraocular lens.

The optic part (The first part) FIG. 2 may use the same materials and the same characteristics used in the ordinary intraocular lenses.

Figure 3:
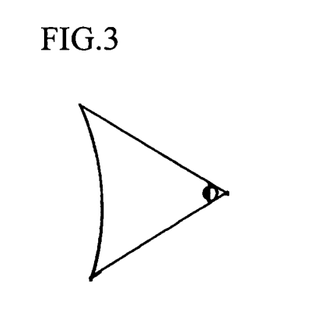
FIG. 3: The second part of the modified intraocular lens.
Figure 14:
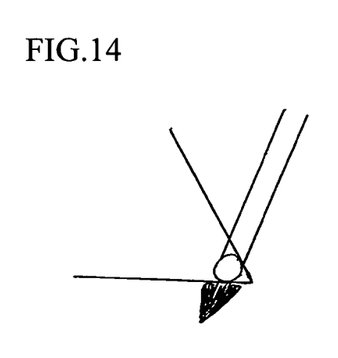
FIG. 14: A male buckle member wedge's tip fastened into a female buckle member haptic of the lens.
Figure 15:
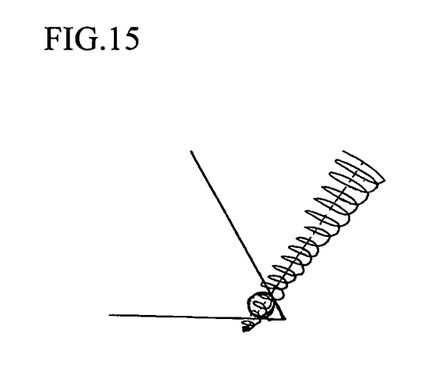
FIG. 15: A screw wedge's tip with an external thread fastened into a haptic hole with an internal thread.
Figure 16:
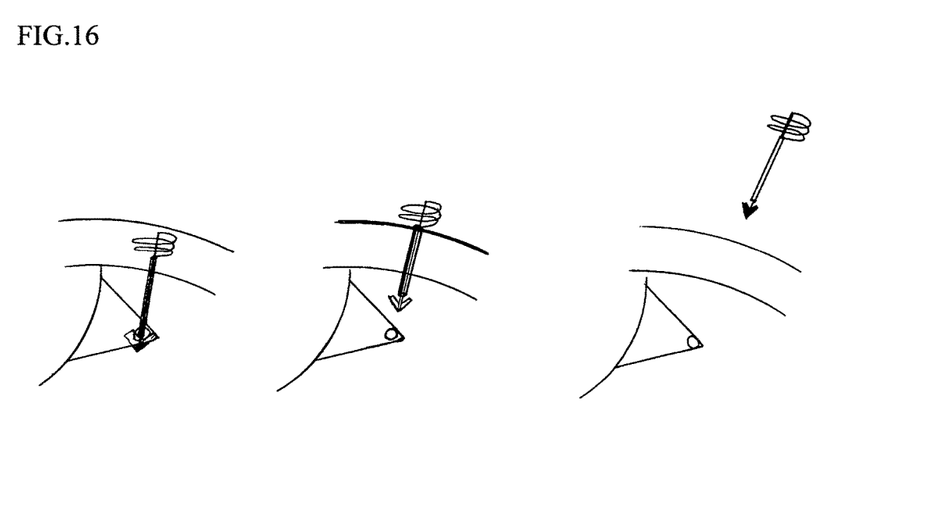
FIG. 16: Corneal/limbal fixation steps—fixation for each modified haptic at a time.

The modified haptic, plate-haptic or arm (The second part) FIG. 3 uses the same materials and characteristics used in the ordinary intraocular lenses but it is modified so it can receive the tip of the corneal/limbal wedge (Elias wedge) that will attach to it, so the modified haptic has a small hole that correlates and fits the corneal/limbal wedge's tip. The hole in the haptic could be a nut-shaped (has an internal thread) to fit a screw tip FIG. 15 or a female buckle member (the catch end) to fit a male buckle member tip (the hook end) FIG. 14, or any receiving design to make a fastening system with the tip of the corneal/limbal wedge.

The modified intraocular lens could have two, three or as many haptics as needed to stabilize the lens. The modified intraocular lens could be foldable or non-foldable lens, could be aphakic, phakic or pseudophakic intraocular lens, and could be angle-supported anterior chamber intraocular lens with receiving design for the corneal/limbal wedge.

Figure 4:
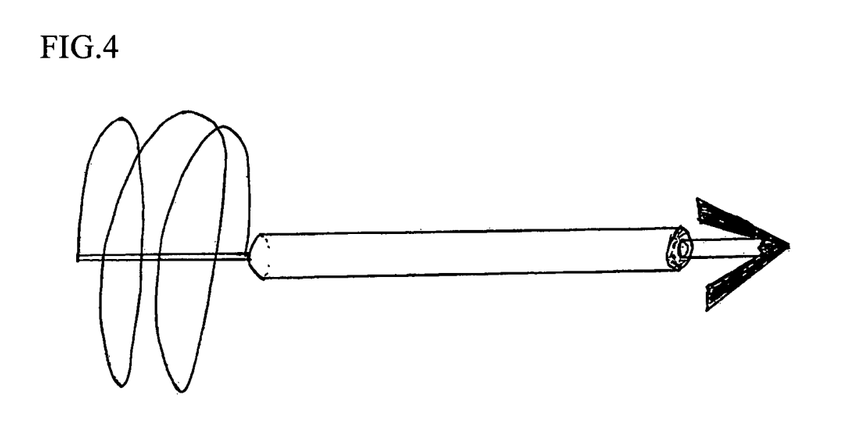
FIG. 4: Corneal/limbal wedge (Elias wedge).

Second: the corneal/limbal wedge (Elias wedge) FIG. 4, which has three parts: base, shaft and tip.

Figure 5:
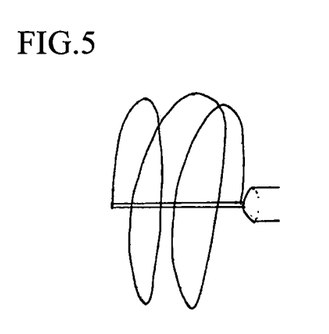
FIG. 5: The first part—Corneal/limbal wedge's base.

Corneal/limbal wedge's base FIG. 5, which lodges in the corneal stroma or the limbus. It stabilizes the whole structure of the wedge by preventing its movement, and at the same time it induces or causes minimal or no stretching to the cornea or the limbus. The base could be designed in many shapes such as spiral screw shape, plate shape, wire shape or any shape that fulfills stabilization of the wedge and that causes minimal stretching of the adjacent structure.

Figure 6:
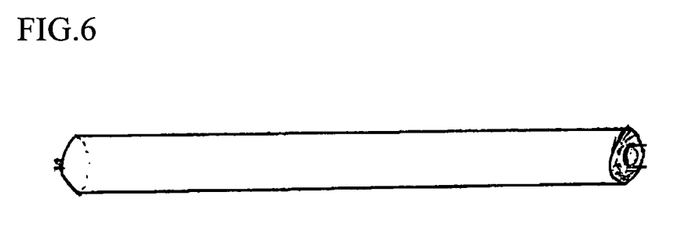
FIG. 6: The second part—Corneal/limbal wedge's shaft.

Corneal/limbal wedge's shaft FIG. 6 could be designed in many shapes: cylindrical shape, plate shape, or any shape that strengthens the shaft and prevents its bending.

Figure 7:
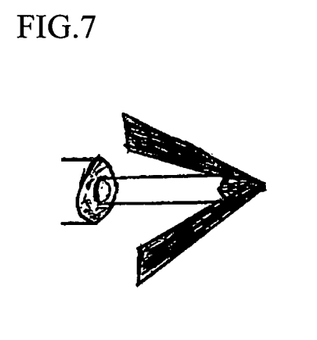
FIG. 7: The third part—Corneal/limbal wedge's tip.

Corneal/limbal wedge's tip FIG. 7 could be designed in many shapes to correlate and fit the receiving part of the modified haptic, so together they will make a strong and stable fastening system, such as a screw shape (external thread) or a male buckle member shape (the hook end).

Figure 17:
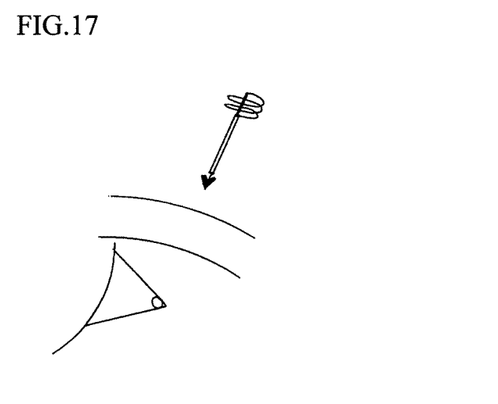
FIG. 17: Orienting the corneal/limbal wedge in the desired direction.
Figure 18:
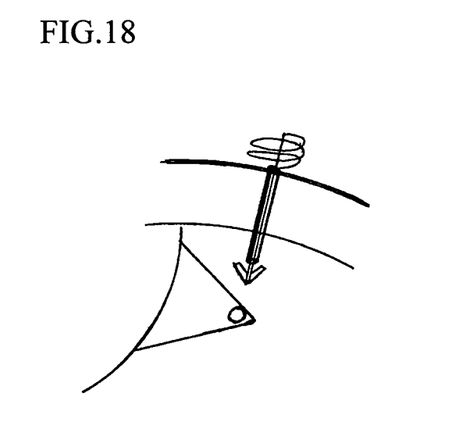
FIG. 18: Inserting the tip, and the shaft through the whole thickness of the cornea, or the limbus, till the spiral-shaped base just touch the anterior surface of the cornea or the limbus.
Figure 19:
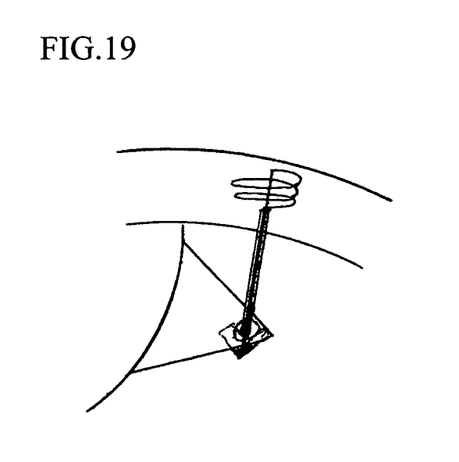
FIG. 19: Torque the spiral-shaped base till it entered completely inside the cornea or the limbus.

The implantation of the modified intraocular lens into the anterior chamber is done by using any of the ordinary processes for intraocular lens implantation in cataract surgery, after that we place the implanted lens in the needed position, then the corneal/limbal wedges (Elias wedges) are implanted as follows: Orient the corneal/limbal wedge in the desired direction FIG. 17, which is guided with the position of the implanted lens' haptic or could be set previously in determined places on the corneal/limbal surface, then insert the tip, and the shaft through the whole thickness of the cornea, or the limbus, till the spiral-shaped base just touch the anterior surface of the cornea or the limbus FIG. 18, then torque the spiral-shaped base till it entered completely inside the cornea or the limbus FIG. 19. In order to torque the spiral-shaped base, we may use a screwdriver and modify the wedge's base so it fits the screwdriver. If the base of the wedge isn't a spiral-shaped then we just push it inside the stroma of the cornea or the limbus. During or after the insertion of the corneal/limbal wedges one at a time in the desired places, the fastening or the lock system is connected between each corneal/limbal wedge and its correlated haptic, using any tight fastening systems such as a screw tip (external thread) fastened into a haptic hole with an internal thread FIG. 15 or as a male buckle member tip (the hook end) lodged into a female buckle member (the catch end) FIG. 14. When all implanted wedges are attached to their correlated haptics, we will get a fixated and stabilized intraocular lens FIG. 20 and FIG. 21.

Figure 20:
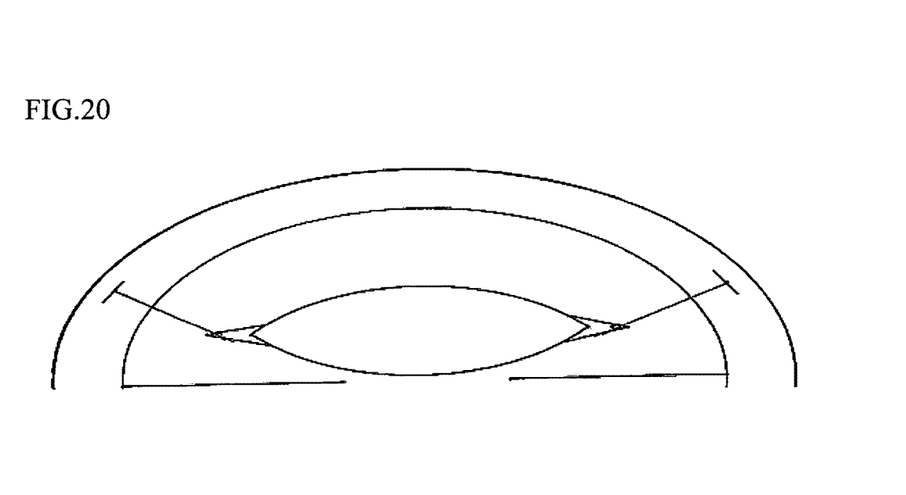
FIG. 20: Cross section for a modified anterior chamber intraocular lens fixated using corneal/limbal wedges.
Figure 21:
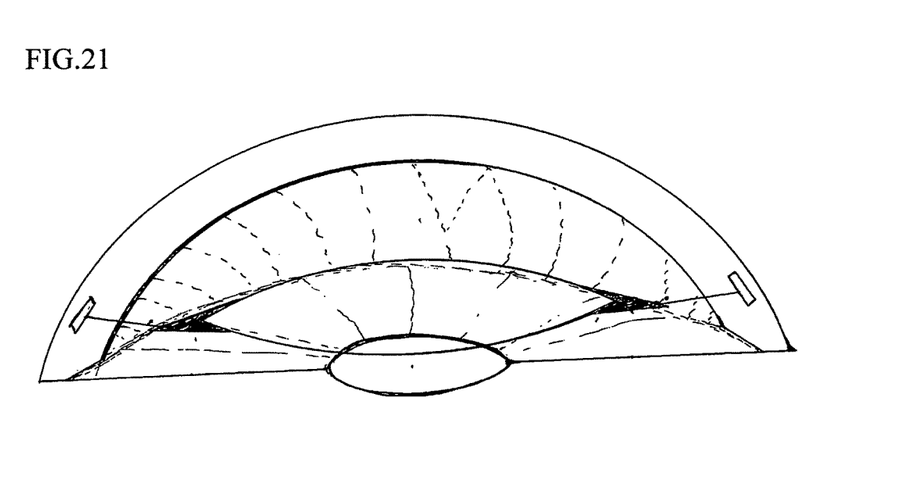
FIG. 21: Cross section of corneal/limbal fixated intraocular lens.

The FIGS. 20 and 21 illustrate cross sections that show the connection between the modified intraocular lens' haptics and the tips of the corneal/limbal wedges with their bases lodged inside the corneal stroma. These figures illustrates the fixed distance between an intraocular lens and cornea which prevents any mechanical damage to the corneal endothelium, furthermore they illustrates the fixed orientation of the optic part of an intraocular lens that helps to manage many refractive problems accurately.

Figure 8:
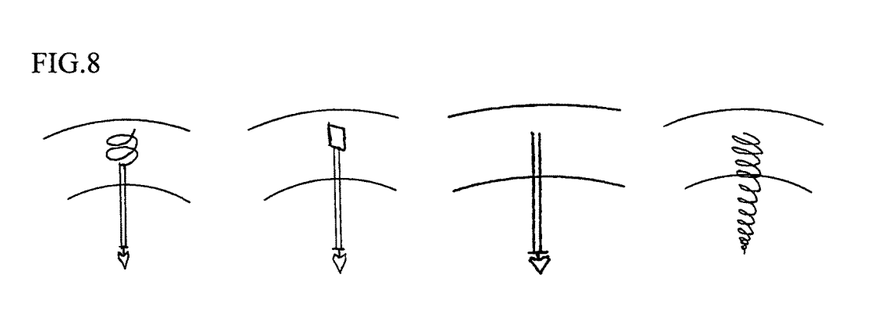
FIG. 8: Different designs and shapes of the corneal/limbal wedges.
Figure 9:
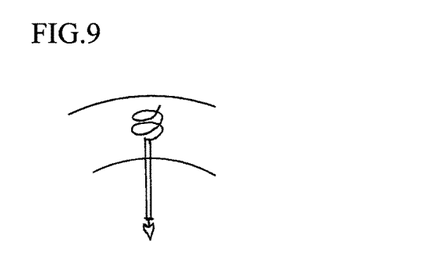
FIG. 9: Spiral-shaped base, cylindrical shaft and male buckle member tip.
Figure 10:
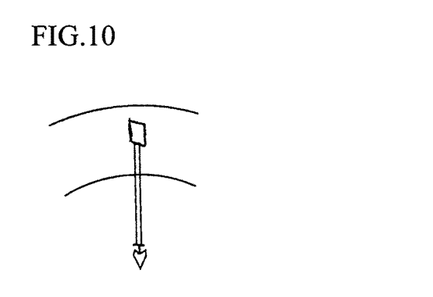
FIG. 10: Plate-shaped base, cylindrical shaft and male buckle member tip.
Figure 11:
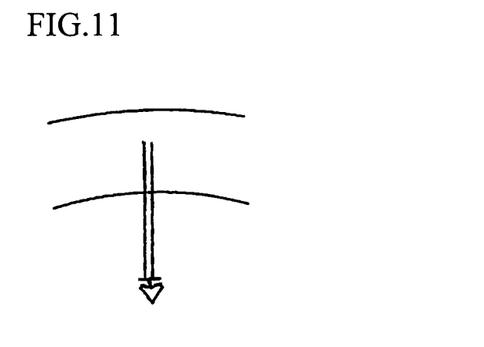
FIG. 11: Cylindrical base, cylindrical shaft and male buckle member tip.
Figure 12:
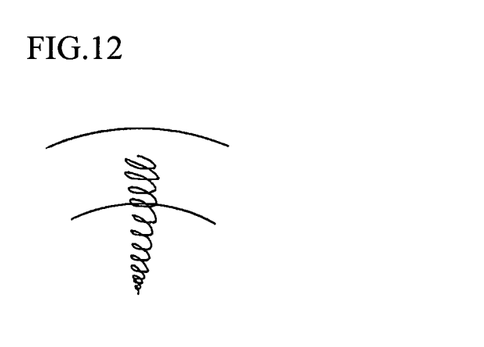
FIG. 12: Spiral screw-shaped base, shaft and tip.
Figure 13:
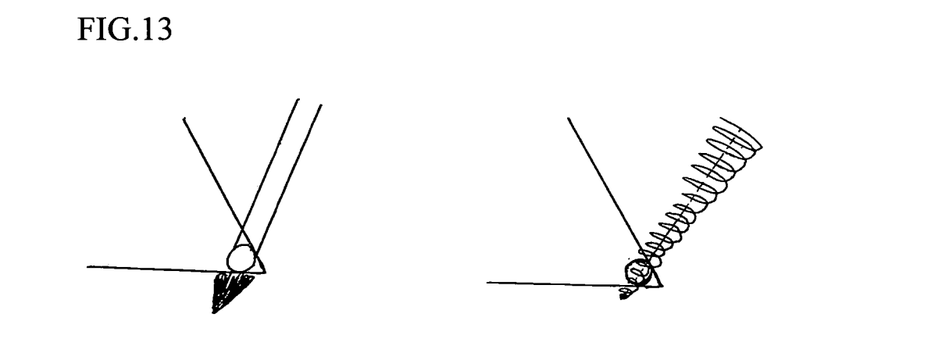
FIG. 13: The fastening system between the tip of the corneal/limbal wedge and the haptic of the modified intraocular lens.

The corneal/limbal wedge could have different designs and shapes as shown in FIG. 8:

The two curved lines represent the cross section of the cornea of the eye.

This is the position of the corneal/limbal wedge after implanting or inserting it through the cornea or the limbus from outside till the base of the wedge entirely lodges inside the cornea or the limbus.

FIG. 9, FIG. 10, FIG. 11 and FIG. 12 illustrate possible designs and shapes of corneal/limbal wedge (Elias wedge).

The invention claimed is:

1. A method of fixating an intraocular lens into the eye comprising: inserting a foldable intraocular lens with a haptic that comprises an aperture into the anterior chamber of the eye by injecting it through a corneal incision; placing the inserted intraocular lens in a desired position; inserting and implanting a wedge structure by connecting the wedged structure to the haptic portion of the intraocular lens; wherein the wedge comprises: a plate-shaped base, a cylindrical shaft and a hook-shaped tip; wherein the method of insertion comprises: inserting the hook shaped tip and the cylindrical shaft of the wedge through the entire thickness of the cornea; lodging the plate shaped base of the wedge inside the cornea; and fastening the tip of the wedge into the aperture in the haptic.

* * * * *